United States Patent [19]

Anton et al.

[11] Patent Number: 5,135,860
[45] Date of Patent: Aug. 4, 1992

[54] PROCESS FOR PREPARING GLYOXYLIC ACID/AMINOMETHYLPHOSPHONIC ACID MIXTURES

[75] Inventors: David L. Anton; Robert DiCosimo, both of Wilmington, Del.; Earnest W. Porta, Landenberg, Pa.

[73] Assignee: E. I. Du Pont de Nemours and Company, Wilmington, Del.

[21] Appl. No.: 788,683

[22] Filed: Nov. 6, 1991

[51] Int. Cl.$^5$ .......................... C12P 7/40; C12P 13/00; C12N 9/04

[52] U.S. Cl. .................................... 435/136; 435/128; 435/190

[58] Field of Search ........................ 435/136, 190, 128

[56] References Cited

U.S. PATENT DOCUMENTS 4,233,452  11/1980  Williams et al. ................... 549/79
4,455,371  6/1984  Richardson et al. ................ 435/189

OTHER PUBLICATIONS

Tolbert et al. "J. Biol. Chem." vol. 181, pp. 905-914 (1949).
Zelitch et al, "J. Biol Chem." vol. 201, pp. 707-718 (1953).
Richardson et al. "J. Bio. Chem." vol. 178 pp. 977-987 (1949).

Primary Examiner—Herbert J. Lilling
Attorney, Agent, or Firm—Robert B. Stevenson

[57] ABSTRACT

The invention provides a process for producing mixtures of glyoxylic acid and aminomethylphosphonic acid. The process comprises reacting glycolic acid and oxygen in an aqueous solution in the presence of aminomethylphosphonic acid catalyst consisting of glycolate oxidase and catalase. The resulting mixtures are useful intermediates in the production of N-(phosphonomethyl)glycine.

9 Claims, No Drawings

PROCESS FOR PREPARING GLYOXYLIC ACID/AMINOMETHYLPHOSPHONIC ACID MIXTURES

BACKGROUND OF THE INVENTION

1. Field of the Invention

This invention relates to a process for the production of mixtures of glyoxylic acid and aminomethylphosphonic acid (AMPA), where glycolic acid and oxygen are reacted in an aqueous solution, in the presence of AMPA and catalysts consisting of glycolate oxidase ((S)-2-hydroxy-acid oxidase, EC 1.1.3.15) and catalase (EC 1.11.1.6). The resulting mixtures of glyoxylic acid and AMPA produced in this manner are useful intermediates in the production of N-(phosphonomethyl)glycine, a broad-spectrum, post-emergent phytotoxicant and herbicide useful in controlling the growth of a wide variety of plants.

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide:

$$HOCH_2CO_2H + O_2 \rightarrow OCHCO_2H + H_2O_2$$

N. E. Tolbert et al., *J. Biol. Chem.*, Vol. 181, 905-914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3-40 mM (millimolar). The optimum pH for the glycolate oxidation was reported to be 8.9. Oxalic acid (100 mM) was reported to inhibit the catalytic action of the glycolate oxidase. Similarly, K. E. Richardson and N. E. Tolbert, *J. Biol. Chem.*, Vol. 236, 1280-1284 (1961) showed that buffers containing tris(hydroxymethyl)aminomethane (TRIS) inhibited the formation of oxalic acid in the glycolate oxidase catalyzed oxidation of glycolic acid. C. O. Clagett, N. E. Tolbert and R. H. Burris, *J. Biol. Chem.*, Vol. 178, 977-987 (1949) reported that the optimum pH for the glycolate oxidase catalyzed oxidation of glycolic acid with oxygen was about 7.8-8.6, and the optimum temperature was 35°-40° C.

I. Zelitch and S. Ochoa, *J. Biol. Chem.*, Vol. 201, 707-718 (1953), and J. C. Robinson et al., *J. Biol. Chem.*, Vol. 237, 2001-2009 (1962), reported that the formation of formic acid and $CO_2$ in the spinach glycolate oxidase-catalyzed oxidation of glycolic acid resulted from the nonenzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. The addition of FMN (flavin mononucleotide) was also found to greatly increase the stability of the glycolate oxidase.

N. A. Frigerio and H. A. Harbury, *J. Biol. Chem.*, Vol. 231, 135-157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of FMN (flavin mononucleotide) to solutions of the enzyme greatly increased its stability, and high protein concentrations or high ionic strength maintained the enzyme as octamers or tetramers.

There are numerous other references to the oxidation of glycolic acid catalyzed by glycolic acid oxidase. The isolation of the enzyme (and an assay method) are described in the following references: I. Zelitch, *Methods in Enzymology*, Vol. 1, Academic Press, New York, 1955, p. 528-532 (from spinach and tobacco leaves), M. Nishimura et al., *Arch. Biochem. Biophys.*, Vol. 222, 397-402 (1983) (from pumpkin cotyledons), H. Asker and D. Davies, *Biochim. Biophys. Acta*, Vol. 761, 103-108 (1983) (from rat liver), and M. J. Emes and K. H. Erismann, *Int. J. Biochem.*, Vol. 16, 1373-1378 (1984) (from *Lemna Minor L*). The structure of the enzyme has also been reported: E. Cederlund et al., *Eur. J. Biochem.*, Vol. 173, 523-530 (1988), and Y. Lindquist and C. Branden, *J. Biol. Chem.*, Vol. 264, 3624-3628, (1989).

SUMMARY OF THE INVENTION

This invention relates to the preparation of mixtures of glyoxylic acid (or a salt thereof) and aminomethylphosphonic acid (AMPA) (or a salt thereof), by oxidizing glycolic acid with oxygen in aqueous solution and in the presence of AMPA and two enzyme catalysts, glycolate oxidase ((S)-2-hydroxy-acid oxidase, EC 1.1.3.15) and catalase (EC 1.11.1.6). Such mixtures of glyoxylic acid and AMPA are useful for the preparation of N-(phosphonomethyl)glycine, a post-emergent phytotoxicant and herbicide.

Although the enzyme-catalyzed reaction of glycolic acid with oxygen is well known, high selectivies to glyoxylic acid have not been previously obtained, and there are no previous reports of performing the enzymatic oxidation of glycolic acid in the presence of aminomethylphosphonic acid (AMPA). A previous application, U.S. Ser. No. 07/422,011, filed Oct. 16, 1989, now abandoned, "Production of Glyoxylic Acid from Glycolic Acid", described a process for the enzymatic conversion of glycolic acid to glyoxylic acid in the presence of oxygen, an amine buffer, and the soluble enzymes glycolate oxidase and catalase. This process demonstrated the unexpected synergistic effect of using both catalase (to destroy byproduct hydrogen peroxide) and an amine buffer capable of forming a chemical adduct with the glyoxylic acid produced (limiting its further oxidation). Neither the separate addition of catalase nor an amine buffer was found to produce the high selectivity observed when both were present, and the almost quantitative yields of glyoxylic acid obtained were more than expected from a simple additive effect of using catalase or amine buffer alone.

Improvements in the yields of glyoxylate produced by the formation of an oxidation-resistant complex of glyoxylate and an amine buffer (via the formation of an N-substituted hemiaminal and/or imine) were found to be dependent on the pKa of the protonated amine buffer. The result of oxidizing aqueous solutions of glycolic acid (0.25M) in the presence of an amine buffer (0.33 M, pH 8.3), glycolate oxidase (0.5 IU/mL), catalase (1,400 IU/mL), and FMN (0.01 mM) at 30° C., and under 1 atm of oxygen for 24 h, are listed in the table below, along with reactions performed using two buffers not expected to complex with glyoxylate (phosphate and bicine):

| Buffer (pKa) | % oxylate | % glyoxylate | % glycolate | % formate |
|---|---|---|---|---|
| ethylenediamine (6.85, 9.93) | 6.8 | 85.5 | 0.8 | 2.4 |
| TRIS (8.08) | 1.1 | 81.0 | 2.8 | 12.0 |
| methylamine (10.62) | 1.0 | 53.9 | 39.8 | 5.1 |
| ethanolamine (9.50) | 1.8 | 69.6 | 4.81 | 24.5 |
| ammonium chloride (9.24) | 1.1 | 39.9 | 37.7 | 18.9 |
| isopropanolamine (9.43) | 2.0 | 60.0 | 4.8 | 37.4 |
| bicine (8.30) | 1.0 | 24.9 | 25.6 | 43.8 |
| phosphate (2.15, 7.10, 12.3) | 0.7 | 24.5 | 52.4 | 21.2 |

Of the amine buffers examined, amines with a pKa approximately equal to or lower than the pH of the reaction mixture (i.e., ethylenediamine and tris) produced much higher yields of glyoxylate (and low formate and oxalate production) than amine buffers whose pKa's were higher than the pH at which the reaction was performed. These results are consistent with the expectation that an unprotonated amine may be necessary to form an oxidation-resistant N-substituted hemiaminal and/or imine complex with glyoxylate; an amine buffer whose pKa is much higher than the pH of the reaction mixture would be present predominantly as the protonated ammonium ion in the reaction mixture, and therefore be less likely to form such complexes with glyoxylate.

The pKa of the protonated amine of aminomethylphosphonic acid (AMPA) is reported to be 10.8 (Lange's Handbook of Chemistry, J. A. Dean, Ed., McGraw-Hill, New York, 1979, 12th Edition), therefore it was unexpected that the addition of AMPA to enzymatic oxidations of glycolic acid within the pH range of 7 to 9 would result in high yields of glyoxylic acid. The accompanying Examples illustrate that yields of glyoxylic acid as high as 92% have been attained using this amine. In addition to the unexpected high yields of glyoxylic acid obtained, the use of AMPA also results in an improvement in recovery of glycolate oxidase and catalase activity when compared to reactions run in the absence of added AMPA (Example 13). Recovery of catalyst for recycle is usually required in processes utilizing enzyme catalysts, where catalyst cost makes a significant contribution to the total cost of manufacture.

DESCRIPTION OF THE PREFERRED EMBODIMENTS

The catalytic oxidation of glycolic acid or a suitable salt thereof is conveniently carried out by contacting the glycolic acid with a source of molecular oxygen in the presence of an enzyme catalyst which catalyzes the reaction of glycolic acid with $O_2$ to form glyoxylic acid. One such catalyst is the enzyme glycolate oxidase (EC 1.1.3.15), also known as glycolic acid oxidase. Glycolate oxidase may be isolated from numerous sources well-known to the art. The glycolate oxidase used in the reaction should be present in an effective concentration, usually a concentration of about 0.01 to about 1000 IU/mL, preferably about 0.1 to about 4 IU/mL. An IU (International Unit) is defined as the amount of enzyme that will catalyze the transformation of one micromole of substrate per minute. A procedure for the assay of this enzyme is found in I. Zelitch and S. Ochoa, J. Biol. Chem., Vol. 201, 707–718 (1953). This method is also used to assay the activity of recovered or recycled glycolate oxidase.

Optimal results in the use of glycolate oxidase as a catalyst for the oxidative conversion of glycolic acid to glyoxylic acid are obtained by incorporating into the reaction solution a catalyst for the decomposition of hydrogen peroxide. One such peroxide-destroying catalyst which is effective in combination with glycolate oxidase is the enzyme catalase (E.C. 1.11.1.6). Catalase catalyzes the decomposition of hydrogen peroxide to water and oxygen, and it is believed to improve yields of glyoxylic acid in the present process by accelerating the decomposition of the hydrogen peroxide produced along with glyoxylic acid in the glycolate oxidase-catalyzed reaction of glycolic acid with $O_2$. The concentration of catalase should be 50 to 50,000 IU/mL, preferably 500 to 15,000 IU/mL. It is preferred that the catalase and glycolate oxidase concentrations be adjusted within the above ranges so that the ratio (measured in IU for each enzyme) of catalase to glycolate oxidase is at least about 250:1.

Another optional but often beneficial ingredient in the reaction solution is flavin mononucleotide (hereinafter referred to as FMN) which is generally used at a concentration of 0.0 to about 2.0 mM, preferably about 0.01 to about 0.2 mM. It is believed the FMN increases the productivity of the glycolate oxidase, by which is meant the amount of glycolic acid converted to glyoxylic acid per unit enzyme increases. It is to be understood that the concentration of added FMN is in addition to any FMN present with the enzyme, because FMN is often also added to the enzyme during the preparation of the enzyme. The structure of FMN and a method for its analysis is found in K. Yagai, Methods of Biochemical Analysis, Vol. X, Interscience Publishers, New York, 1962, p. 319–355, which is hereby included by reference.

Glycolic acid (2-hydroxyacetic acid) is available commercially. In the present reaction its initial concentration is in the range of 0.10M to 2.0M, preferably between 0.25M and 1.0M. It can be used as such or as a compatible salt thereof, that is, a salt that is water-soluble and whose cation does not interfere with the desired conversion of glycolic acid to glyoxylic acid, or the subsequent reaction of the glyoxylic acid product with the aminomethylphosphonic acid to form N-(phosphonomethyl)glycine. Suitable and compatible salt-forming cationic groups are readily determined by trial. Representative of such salts are the alkali metal, alkaline earth metal, ammonium, substituted ammonium, phosphonium, and substituted phosphonium salts.

The conversion of glycolic acid to glyoxylic acid is conveniently and preferably conducted in aqueous media. Aminomethylphosphonic acid (AMPA), or a suitable salt thereof, is added to produce a molar ratio of AMPA/glycolic acid (starting amount) in the range of from 0.01/1.0 to 3.0/1.0, preferably from 0.25/1.0 to 1.05/1.0. After combining AMPA and glycolic acid in an aqueous solution, the pH of the resulting mixture is adjusted to a value between 6 and 10, preferably between 7.0 and 8.5. Within this pH range, the exact value may be adjusted to obtain the desired pH by adding any compatible, non-interfering base, including alkali metal hydroxides, carbonates, bicarbonates and phosphates. The pH of the reaction mixture decreases slightly as the reaction proceeds, so it is often useful to start the reaction near the high end of the maximum enzyme activity pH range, about 9.0–8.5, and allow it to drop during the reaction. The pH can optionally be maintained by the separate addition of a non-interfering inorganic or organic buffer, since enzyme activity varies with pH.

It is understood that glycolic and glyoxylic acids are highly dissociated in water, and at pH of between 7 and 10 are largely if not substantially entirely present as glycolate and glyoxylate ions. It will also be appreciated by those skilled in the art that glyoxylic acid (and its conjugate base, the glyoxylate anion) may also be present as the hydrate, e.g. $(HO)_2CHCOOH$ and/or as the hemiacetal, $HOOCCH(OH)OCH(OH)COOH$, which compositions and their anionic counterparts are equivalent to glyoxylic acid and its anion for the present purpose of being suitable reactants for N-(phosphonomethyl)glycine formation.

Oxygen $(O_2)$, the oxidant for the conversion of the glycolic acid to glyoxylic acid, may be added as a gas to the reaction by agitation of the liquid at the gas-liquid interface or through a membrane permeable to oxygen. It is believed that under most conditions, the reaction rate is at least partially controlled by the rate at which oxygen can be dissolved into the aqueous medium. Thus, although oxygen can be added to the reaction as air, it is preferred to use a relatively pure form of oxygen, and even use elevated pressures. Although no upper limit of oxygen pressure is known, oxygen pressures up to 50 atmospheres may be used, and an upper limit of 15 atmospheres is preferred. Agitation is important to maintaining a high oxygen dissolution (hence reaction) rate. Any convenient form of agitation is useful, such as stirring. On the other hand, as is well known to those skilled in the enzyme art, high shear agitation or agitation that produces foam may decrease the activity of the enzyme(s), and should be avoided.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction. The temperature should not be so low that the aqueous solution starts to freeze. Temperature can be controlled by oridinary methods, such as, but not limited to, by using a jacketed reaction vessel and passing liquid of the appropriate temperature through the jacket. The reaction vessel may be constructed of any material that is inert to the reaction ingredients.

Upon completion of the reaction, the enzymes may be removed by filtration or centrifugation and reused. Alternatively, they can be denatured and precipitated by heating, e.g. to 70° C. for 5 minutes, and/or can be allowed to remain in the reaction mixture if their presence in the subsequent steps of converting the glyoxylic acid-aminomethylphosphonic acid mixture to N-(phosphonomethyl)glycine, and of recovering N-(phosphonomethyl)glycine from the reaction mixture, is not objectionable.

Following the cessation of contacting the reaction solution with $O_2$, and preferably following the removal of the enzyme glycolate oxidase and the enzyme catalase when present, flavin mononucleotide (FMN) may optionally be removed by contacting the solution with decolorizing carbon. The solution containing glyoxylic acid and aminomethylphosphonic acid (which are believed to be in equilibrium with the corresponding imine), is treated in accordance with any of the processes known to the art for producing N-(phosphonomethyl)glycine.

Catalytic hydrogenation is a preferred method for preparing N-(phosphonomethyl)glycine from a mixture of glyoxylic acid and aminomethylphosphonic acid. Hydrogenation catalysts suitable for this purpose include (but are not limited to) the various platinum metals, such as iridium, osmium, rhodium, ruthenium, platinum, and palladium; also various other transition metals such as cobalt, copper, nickel and zinc. The catalyst may be unsupported, for example as Raney nickel or platinum oxide; or it may be supported, for example as platinum on carbon, palladium on alumina, or nickel on kieselguhr. Palladium on carbon, nickel on kieselguhr and Raney nickel are preferred. The hydrogenation can be performed at a pH of from 4 to 11, preferably from 5 to 10. The hydrogenation temperature and pressure can vary widely. The temperature is generally in the range of 0° C. to 150° C., preferably from 20° C. to 90° C., while the $H_2$ pressure is generally in the range of from about atmospheric to about 100 atmospheres, preferably from 1 to 10 atmospheres. N-(Phosphonomethyl)glycine, useful as a post-emergent herbicide, may be recovered from the reduced solution, whatever the reducing method employed, by any of the recovery methods known to the art.

In the following examples, which serve to further illustrate the invention, the yields of glyoxylate, formate and oxalate, and the recovered yield of glycolate, are percentages based on the total amount of glycolic acid present at the beginning of the reaction. Analyses of reaction mixtures were performed using high pressure liquid chromatography. Organic acid analyses were performed using a Bio-Rad HPX-87H column, and AMPA and N-(phosphonomethyl)glycine were analyzed using a Bio-Rad Aminex glyphosate analysis column.

EXAMPLE 1

Into a 3 oz. Fischer-Porter glass aerosol reaction vessel was placed a magnetic stirring bar and 10 mL of an aqueous solution containing glycolic acid (0.25M), aminomethylphosphonic acid (AMPA, 0.263M), FMN (0.01 mM), propionic acid (HPLC internal standard, 0.125M), glycolate oxidase (from spinach, 1.0 IU/mL), and catalase (from *Aspergillus niger*, 1,400 IU/mL) at pH 8.5. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psig of oxygen and the mixture stirred at 15° C. Aliquots (0.10 mL) were removed by syringe through a sampling port (without loss of pressure in the vessel) at regular intervals for analysis by HPLC to monitor the progress of the reaction. After 5 h, the HPLC yields of glyoxylate, formate, and oxalate were 70.4%, 19.6%, and 2.2%, respectively, and 5.3% glycolate remained. The remaining activity of glycolate oxidase and catalase were 27% and 100%, respectively, of their initial values.

Example 2 (Comparative)

The reaction in Example 1 was repeated, using 0.33 M $K_2HPO_4$ in place of 0.265M AMPA. After 5 h, the HPLC yields of glyoxylate, formate, and oxalate were 34.1%, 11.1%, and 0.2%, respectively, and 58.7% glycolate remained. After 23 h, the HPLC yields of glyoxylate, formate, and oxalate were 39.4%, 44.7%, and 15.34%, respectively, and no glycolate remained. The remaining activity of glycolate oxidase and catalase were 85% and 87%, respectively, of their initial values.

Example 3 (Comparative)

The reaction in Example 1 was repeated, using 0.263M bicine buffer in place of 0.265M AMPA. After 5 h, the HPLC yields of glyoxylate, formate, and oxalate were 42.5%, 49.6%, and 10.1%, respectively, and 0.2% glycolate remained. The remaining activity of glycolate oxidase and catalase were 47% and 100%, respectively, of their initial values.

EXAMPLE 4

The reaction in Example 1 was repeated using 5,600 IU/mL catalase from *Aspergillus niger*. After 6 h, the HPLC yields of glyoxylate, formate, and oxalate were 85.5%, 7.6%, and 3.3%, respectively, and 2.5% glycolate remained. The remaining activity of glycolate oxidase and catalase were 36% and 100%, respectively, of their initial values.

EXAMPLE 5

The reaction in Example 1 was repeated using 14,000 IU/mL catalase from *Aspergillus niger*. After 6 h, the HPLC yields of glyoxylate, formate, and oxalate were 88.0%, 3.3%, and 3.0%, respectively, and 3.4% glycolate remained. The remaining activity of glycolate oxidase and catalase were 28% and 96%, respectively, of their initial values.

EXAMPLE 6

The reaction in Example 1 was repeated using 56,000 IU/mL catalase from *Aspergillus niger*. After 6 h, the HPLC yields of glyoxylate, formate, and oxalate were 84.0%, 0.4%, and 2.5%, respectively, and 8.4% glycolate remained. The remaining activity of glycolate oxidase and catalase were 16% and 76%, respectively, of their initial values.

EXAMPLE 7

Into a 3 oz. Fischer-Porter glass aerosol reaction vessel was placed a magnetic stirring bar and 10 mL of an aqueous solution containing glycolic acid (0.25M), aminomethylphosphonic acid (AMPA, 0.20M), FMN (0.01 mM), butyric acid (HPLC internal standard, 0.10M), glycolate oxidase (from spinach, 1.0 IU/mL), and catalase (from *Aspergillus niger*, 14,000 IU/mL) at pH 8.5. The reaction vessel was sealed and the reaction mixture was cooled to 5° C. (instead of 15° C. as described in previous examples), then the vessel was flushed with oxygen by pressurizing to 70 psig and venting to atmospheric pressure five times with stirring. The vessel was then pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 6 h, the HPLC yields of glyoxylate, formate, and oxalate were 92.3%, 4.36%, and 5.5%, respectively, and no glycolate remained. The remaining activity of glycolate oxidase and catalase were 87% and 88%, respectively, of their initial values.

EXAMPLE 8

The reaction in Example 7 was repeated, using an aqueous solution containing glycolic acid (0.50M), aminomethylphosphonic acid (AMPA, 0.40M), FMN (0.01 mM), butyric acid (HPLC internal standard, 0.10M), glycolate oxidase (from spinach, 1.0 IU/mL), and catalase (from *Aspergillus niger*, 14,000 IU/mL) at pH 8.5. After 17.5 h, the HPLC yields of glyoxylate, formate, and oxalate were 91.0%, 2.9%, and 2.9%, respectively, and 4.1% glycolate remained. The remaining activity of glycolate oxidase and catalase were 63% and 91%, respectively, of their initial values.

EXAMPLE 9

The reaction in Example 7 was repeated, using an aqueous solution containing glycolic acid (0.75M), aminomethylphosphonic acid (AMPA, 0.60M), FMN (0.01 mM), butyric acid (HPLC internal standard, 0.10M), glycolate oxidase (from spinach, 2.0 IU/mL), and catalase (from *Aspergillus niger*, 14,000 IU/mL) at pH 8.5.. After 40 h, the HPLC yields of glyoxylate, formate, and oxalate were 83.2%, 2.3%, and 7.5%, respectively, and no glycolate remained. The remaining activity of glycolate oxidase and catalase were 65% and 86%, respectively, of their initial values.

EXAMPLE 10

The reaction in Example 7 was repeated, using an aqueous solution containing glycolic acid (1.0M), aminomethylphosphonic acid (AMPA, 0.80M), FMN (0.01 mM), butyric acid (HPLC internal standard, 0.01M), glycolate oxidase (from spinach, 2.0 IU/mL), and catalase (from *Aspergillus niger*, 14,000 IU/mL) at pH 8.5.. After 66 h, the HPLC yields of glyoxylate, formate, and oxalate were 78.9%, 2.2%, and 12.1%, respectively, and 2.0% glycolate remained. The remaining activity of glycolate oxidase and catalase were 64% and 87%, respectively, of their initial values.

EXAMPLE 11

The reaction in Example 8 was repeated at pH 8.0. After 17.5 h, the HPLC yields of glyoxylate, formate, and oxalate were 87.0%, 2.2%, and 1.9%, respectively, and 8.5% glycolate remained. The remaining activity of glycolate oxidase and catalase were 44% and 97%, respectively, of their initial values.

EXAMPLE 12

The reaction in Example 8 was repeated at pH 7. After 17.5 h, the HPLC yields of glyoxylate, formate, and oxalate were 88.0%, 1.4%, and 1.9%, respectively, and 8.2% glycolate remained. The remaining activity of glycolate oxidase and catalase were 44% and 93%, respectively, of their initial values.

EXAMPLE 13

Into a 3 oz. Fischer-Porter glass aerosol reaction vessel was placed a magnetic stirring bar and 10 mL of an aqueous solution containing glycolic acid (0.50M), FMN (0.01 mM), isobutyric acid (HPLC internal standard, 0.10M), glycolate oxidase (from spinach, 1.0 IU/mL), and catalase (from *Aspergillus niger*, 14,000 IU/mL) at pH 8.5. The reaction vessel was sealed and the reaction mixture was cooled to 5° C., then the vessel was flushed with oxygen by pressurizing to 70 psig and venting to atmospheric pressure five times with stirring. The vessel was then pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 21 h, the HPLC yields of glyoxylate, formate, and oxalate were 81.7%, 1.2%, and 2.2%, respectively, and 7.5% glycolate remained. The remaining activity of glycolate oxidase and catalase were 19% and 77%, respectively, of their initial values. This reaction was then repeated with 0.50M glycolic acid and 0.25M, 0.375M, 0.40M, 0.50M, or 0.625M aminomethylphosphonic acid (AMPA) present, and the yields of reaction products and enzyme recoveries for these reactions are listed below:

| [AMPA] (M) | glyoxy-late (%) | for-mate (%) | oxa-late (%) | glyco-late (%) | glycolate oxidase (%) | cata-lase (%) |
|---|---|---|---|---|---|---|
| 0.00 | 81.7 | 1.2 | 2.2 | 7.5 | 19 | 77 |
| 0.25 | 79.4 | 2.1 | 3.3 | 2.5 | 48 | 79 |
| 0.375 | 78.3 | 2.3 | 3.6 | 1.7 | 57 | 95 |
| 0.40 | 91.0 | 2.9 | 2.9 | 4.1 | 63 | 91 |
| 0.50 | 85.2 | 1.5 | 3.3 | 5.5 | 49 | 93 |
| 0.625 | 79.6 | 1.7 | 1.8 | 14.0 | 42 | 94 |

EXAMPLE 14

The mixture of glyoxylic acid (0.46M) and AMPA (0.40M) from Example 8 was filtered using an Amicon Centriprep 10 concentrator (10,000 molecular weight cutoff) to remove the soluble enzymes, then the filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi and stirred at 25° C. After 17 h, the concentration of N-(phosphonomethyl)glycine (determined by HPLC) was 0.29M (72% yield based on AMPA).

We claim:

1. A process for preparing a mixture of glyoxylic acid and aminomethylphosphonic acid comprising the step of oxidizing glycolic acid with oxygen in an aqueous solution, in the presence of aminomethylphosphonic acid and the enzymes glycolate oxidase and catalase.

2. A process of claim 1 wherein said resulting mixture of glyoxylic acid and aminomethylphosphonic acid is capable of being directly converted to N-(phosphonomethyl)glycine.

3. An improved process for preparing a mixture useful as an intermediate for the production of N-(phosphonomethyl)glycine comprising the steps of generating a glyoxylic acid component in situ by incorporating into an aqueous solution of a glycolic acid component and an aminomethylphosphonic acid component, a first catalyst adapted to catalyze the oxidation of glycolic acid component with oxygen to a glyoxylic acid component and hydrogen peroxide, and a second catalyst adapted to catalyze the decomposition of hydrogen peroxide, adjusting the pH of the solution to between 7 and about 10, contacting the solution with a source of oxygen at an effective temperature and sufficient time to convert at least a portion of the glycolic acid component to the glyoxylic acid component in the presence of an aminomethylphosphonic acid component, and ceasing contacting the solution with oxygen prior to converting said intermediate to N-(phosphonomethyl)glycine.

4. The process of claim 3 wherein the first catalyst is glycolate oxidase and the second catalyst is catalase.

5. A process of claim 3 wherein the glycolic acid to glyoxylic acid conversion is performed at a pH between about 8.0 to about 9.5.

6. A process of claim 3 wherein the temperature is carried out at a temperature of from 0° C. to about 40° C.

7. A process of claim 3 wherein flavin mononucleotide is present.

8. A process of claim 4 wherein the concentration of glycolate oxidase is from 0.01 to about 1000 IU/mL.

9. A process of claim 4 wherein the concentration of catalase is from 50 to 50,000 IU/mL.

* * * * *